(12) United States Patent
Jones et al.

(10) Patent No.: US 10,059,916 B2
(45) Date of Patent: *Aug. 28, 2018

(54) REGULATED VACUUM OFF-GASSING OF GAS FILTER FOR FLUID PROCESSING SYSTEM AND RELATED METHODS

(71) Applicant: LIFE TECHNOLOGIES CORPORATION, Carlsbad, CA (US)

(72) Inventors: Nephi D. Jones, Newton, UT (US); Christopher D. Brau, Logan, UT (US)

(73) Assignee: Life Technologies Corporation, Carlsbad, CA (US)

(*) Notice: Subject to any disclaimer, the term of this patent is extended or adjusted under 35 U.S.C. 154(b) by 71 days.

This patent is subject to a terminal disclaimer.

(21) Appl. No.: 15/249,781

(22) Filed: Aug. 29, 2016

(65) Prior Publication Data

US 2016/0362653 A1 Dec. 15, 2016

Related U.S. Application Data

(63) Continuation of application No. 14/508,824, filed on Oct. 7, 2014, now Pat. No. 9,457,306.

(51) Int. Cl.
*B01D 5/00* (2006.01)
*C12M 1/00* (2006.01)
(Continued)

(52) U.S. Cl.
CPC ............ *C12M 29/20* (2013.01); *B01D 5/00* (2013.01); *B01D 19/0005* (2013.01); *B01D 19/0031* (2013.01); *B01D 19/0036* (2013.01); *B01D 46/0002* (2013.01); *B01D 46/002* (2013.01); *B01D 46/446* (2013.01);
(Continued)

(58) Field of Classification Search
CPC .... B01D 53/265; B01D 5/00; B01D 19/0005; B01D 19/0031; B01D 19/0036; B01D 46/0002; B01D 46/002; B01D 46/446; C12M 23/14; C12M 23/26; C12M 29/04;
(Continued)

(56) References Cited

U.S. PATENT DOCUMENTS 3,140,716 A 7/1964 Harrison et al.
3,212,274 A 10/1965 Eidus
(Continued)

FOREIGN PATENT DOCUMENTS

CN 1649654 A 8/2005
CN 2012 76562 A 7/2009
(Continued)

OTHER PUBLICATIONS

International Search Report and Written Opinion dated Jan. 5, 2016, issued in PCT Application No. PCT/US2015/054241, filed Oct. 6, 2015.
(Continued)

*Primary Examiner* — Frank Lawrence
(74) *Attorney, Agent, or Firm* — Workman Nydegger

(57) ABSTRACT

A method for filtering a gas includes delivering a gas into a compartment of a gas filter, the compartment being at least partially bounded by a casing comprised of a flexible sheet of polymeric film. A partial vacuum is applied to the gas filter so that the partial vacuum assists in drawing the gas through a porous filter body of the gas filter that is at least partially disposed within the compartment of the gas filter.

20 Claims, 8 Drawing Sheets

(51) Int. Cl.
*B01D 46/00* (2006.01)
*B01D 46/44* (2006.01)
*B01D 19/00* (2006.01)
*B01D 53/26* (2006.01)
*C12M 1/34* (2006.01)
*C12M 1/36* (2006.01)

(52) U.S. Cl.
CPC .......... *B01D 53/265* (2013.01); *C12M 23/14* (2013.01); *C12M 23/26* (2013.01); *C12M 29/04* (2013.01); *C12M 29/06* (2013.01); *C12M 41/14* (2013.01); *C12M 41/40* (2013.01); *C12M 41/48* (2013.01)

(58) Field of Classification Search
CPC ...... C12M 29/06; C12M 29/20; C12M 41/14; C12M 41/40; C12M 41/48
USPC ........ 95/19, 22, 214, 226; 96/333, 337, 340, 96/342; 55/385.1
See application file for complete search history.

(56) References Cited

U.S. PATENT DOCUMENTS

| | | | |
|---|---|---|---|
| 3,422,887 A | 1/1969 | Berkeley | |
| 3,672,959 A | 6/1972 | Sweet | |
| 4,177,816 A | 12/1979 | Torgeson | |
| 4,182,656 A | 1/1980 | Ahnell et al. | |
| 4,194,950 A | 3/1980 | Zalles | |
| 4,258,784 A | 3/1981 | Perry et al. | |
| 4,309,592 A | 1/1982 | Le Boeuf | |
| 4,561,498 A | 12/1985 | Nowobilski et al. | |
| 4,573,933 A | 3/1986 | Cameron | |
| 4,574,876 A | 3/1986 | Aid | |
| 4,612,086 A | 9/1986 | Dominguez | |
| 4,731,072 A | 3/1988 | Aid | |
| 4,744,414 A | 5/1988 | Schon | |
| 4,797,587 A | 1/1989 | Tschudi et al. | |
| 5,121,857 A | 6/1992 | Hutchinson | |
| 5,243,833 A | 9/1993 | Coelho et al. | |
| 5,245,693 A | 9/1993 | Ford et al. | |
| 5,287,918 A | 2/1994 | Banks et al. | |
| 5,372,621 A | 12/1994 | Staton | |
| 5,381,510 A | 1/1995 | Ford et al. | |
| 5,411,077 A | 5/1995 | Tousignant | |
| 5,443,985 A | 8/1995 | Lu et al. | |
| 5,632,793 A | 5/1997 | Haggard | |
| 5,875,282 A | 2/1999 | Jordan et al. | |
| 6,083,587 A | 7/2000 | Smith et al. | |
| 6,133,021 A | 10/2000 | Gu et al. | |
| 6,391,093 B1 | 5/2002 | French et al. | |
| 6,432,698 B1 | 8/2002 | Gaugler et al. | |
| 6,490,824 B1 | 12/2002 | Maekawa et al. | |
| 6,535,689 B2 | 3/2003 | Augustine et al. | |
| 6,619,054 B1 | 9/2003 | Cargnelli et al. | |
| 6,626,983 B1 | 9/2003 | Cairns | |
| 6,673,098 B1 | 1/2004 | Machold et al. | |
| 6,673,598 B1 | 1/2004 | Akers et al. | |
| 6,882,797 B2 | 4/2005 | Stewart et al. | |
| 7,011,797 B2 | 3/2006 | Bakke | |
| 7,232,457 B2 | 6/2007 | Schmidt et al. | |
| 7,235,402 B2 | 6/2007 | Aubry | |
| 7,289,724 B2 | 10/2007 | Furnrohr et al. | |
| 7,384,783 B2 | 6/2008 | Kunas et al. | |
| 7,394,976 B2 | 7/2008 | Entenman et al. | |
| 7,487,688 B2 | 2/2009 | Goodwin | |
| 7,629,167 B2 | 12/2009 | Hodge et al. | |
| 7,682,067 B2 | 3/2010 | West et al. | |
| 7,722,839 B2 | 5/2010 | Kuzyk | |
| 7,748,438 B2 | 7/2010 | Ghelli et al. | |
| 7,819,934 B2 | 10/2010 | Galliher | |
| 7,831,318 B2 | 11/2010 | Bartee et al. | |
| 7,878,099 B2 | 2/2011 | Loibl | |
| 7,879,599 B2 | 2/2011 | Goodwin et al. | |
| 7,932,078 B2 | 4/2011 | Posseme et al. | |
| 8,381,780 B2 | 2/2013 | Fisher et al. | |
| 8,455,242 B2 | 6/2013 | Staheli et al. | |
| 8,506,198 B2 | 8/2013 | West et al. | |
| 8,603,805 B2 | 12/2013 | Goodwin et al. | |
| 8,623,640 B2 | 1/2014 | Kunas et al. | |
| 8,641,314 B2 | 2/2014 | Thacker et al. | |
| 2001/0039692 A | 1/2001 | Wright et al. | |
| 2001/0024820 A1 | 9/2001 | Mastromatteo et al. | |
| 2002/0131654 A1 | 9/2002 | Smith et al. | |
| 2003/0077466 A1 | 4/2003 | Smith et al. | |
| 2004/0062140 A1 | 4/2004 | Cadogan et al. | |
| 2004/0149127 A1 | 8/2004 | Lyons | |
| 2005/0239198 A1 | 10/2005 | Kunas et al. | |
| 2005/0272146 A1 | 12/2005 | Hodge et al. | |
| 2006/0196501 A1 | 9/2006 | Bibbo et al. | |
| 2006/0240546 A1 | 10/2006 | Goodwin et al. | |
| 2006/0270036 A1 | 11/2006 | Goodwin et al. | |
| 2006/0275894 A1 | 12/2006 | Felder et al. | |
| 2006/0279167 A1 | 12/2006 | Turner | |
| 2007/0275452 A1 | 11/2007 | Yamasaki et al. | |
| 2008/0060216 A1 | 3/2008 | Reilly | |
| 2008/0068920 A1 | 3/2008 | Galliher et al. | |
| 2008/0127832 A1 | 6/2008 | Zhang | |
| 2008/0272146 A1 | 12/2008 | Hodge et al. | |
| 2009/0035856 A1 | 2/2009 | Galliher et al. | |
| 2009/0081742 A1 | 3/2009 | Dunlop et al. | |
| 2009/0087903 A1 | 4/2009 | Belgrader et al. | |
| 2009/0119869 A1 | 5/2009 | Yoo | |
| 2009/0148143 A9 | 6/2009 | Entenman et al. | |
| 2010/0075405 A1 | 3/2010 | Broadley et al. | |
| 2010/0151558 A1 | 6/2010 | Alianell et al. | |
| 2011/0046551 A1 | 2/2011 | Augustine et al. | |
| 2011/0076759 A1 | 3/2011 | Reif et al. | |
| 2011/0188928 A1 | 8/2011 | West et al. | |
| 2011/0198066 A1 | 8/2011 | Starbard | |
| 2011/0207170 A1 | 8/2011 | Niazi | |
| 2011/0207218 A1 | 8/2011 | Staheli et al. | |
| 2011/0258975 A1 | 10/2011 | Lundgren | |
| 2011/0310696 A1 | 12/2011 | Goodwin et al. | |
| 2012/0132548 A1 | 5/2012 | Galliher et al. | |
| 2012/0177533 A1 | 7/2012 | Lee et al. | |
| 2012/0260671 A1 | 10/2012 | Damren et al. | |
| 2013/0082410 A1 | 4/2013 | Goodwin et al. | |
| 2013/0089925 A1 | 4/2013 | Damren et al. | |
| 2013/0101982 A1 | 4/2013 | Goodwin et al. | |
| 2013/0260463 A1 | 10/2013 | Staheli et al. | |
| 2014/0106453 A1 | 4/2014 | Kunas et al. | |
| 2014/0298612 A1 | 10/2014 | Williams et al. | |
| 2015/0265943 A1 | 9/2015 | Brown et al. | |
| 2015/0265958 A1 | 9/2015 | Brown et al. | |

FOREIGN PATENT DOCUMENTS

| | | |
|---|---|---|
| CN | 201396935 Y | 2/2010 |
| DE | 20 2009 006839 U1 | 7/2009 |
| DE | 10 2008 027 638 A1 | 12/2009 |
| EP | 0 400 829 A1 | 12/1990 |
| EP | 1 837 640 A2 | 9/2007 |
| EP | 1 950 281 A1 | 7/2008 |
| EP | 2 065 085 A1 | 6/2009 |
| EP | 2 123 745 A2 | 11/2009 |
| GB | 2491623 A | 12/2012 |
| JP | S59 42884 A | 3/1984 |
| JP | 3-196836 | 8/1991 |
| JP | H-08-501927 | 3/1996 |
| JP | H-09-014837 | 1/1997 |
| JP | H11-333239 | 12/1999 |
| JP | 2002-003505 | 1/2002 |
| JP | 2004-271031 | 9/2004 |
| JP | 2007-534335 | 11/2007 |
| JP | 2009-050838 | 3/2009 |
| JP | 2009-539408 | 11/2009 |
| JP | 2009-291192 | 12/2009 |
| WO | 94/01530 | 1/1994 |
| WO | 2003/092849 A1 | 11/2003 |
| WO | 2006/116139 | 11/2006 |
| WO | 2009/093995 A1 | 7/2009 |
| WO | 2009/146769 A2 | 12/2009 |
| WO | 2011/041508 A1 | 4/2011 |

(56) References Cited

FOREIGN PATENT DOCUMENTS

| WO | 2011/078773 A1 | 6/2011 |
| WO | 2011/110726 A1 | 9/2011 |
| WO | 2012/170878 A2 | 12/2012 |
| WO | 2013/009668 A2 | 1/2013 |
| WO | 2013/032392 A1 | 3/2013 |
| WO | 2013/053779 A1 | 4/2013 |

OTHER PUBLICATIONS

G. Catapano et al., Bioreactor Design and Scale up, Chapter 5 of Cell and Tissue Reaction Engineering, 2009, pp. 173-259.

Minghui Hu et al., Study of an Efficient Temperature Measurement for an Industrial Bioreactor, ScienceDirect, Measure, vol. 44, 2011, pp. 875-880.

Zhiwei Zhou et al., Optimizing of Bioreactor Heat Supply and Material Feeding by Numberical Calculation, ICICIS, 2011, pp. 195-202.

Discovery Scientific Product Liens, Discovery Scientific, http://discoveryscientific.com/products-by-type2/b/mammalian-insect-cell-culture-bioreactor, Apr. 25, 2014, 3 pages.

DASbox Single-Use Vessel, Brochure, DASGIP Information and Process Technology, GMBH, 2012, 2 pages.

REGULATED VACUUM OFF-GASSING OF GAS FILTER FOR FLUID PROCESSING SYSTEM AND RELATED METHODS

CROSS-REFERENCE TO RELATED APPLICATIONS

This application is a continuation of U.S. application Ser. No. 14/508,824, filed Oct. 7, 2014, U.S. Pat. No. 9,457,306, which is incorporated herein by specific reference.

BACKGROUND OF THE INVENTION

1. The Field of the Invention

The present invention relates to fluid processing systems and related gas filtering systems that apply a partial vacuum on a downstream side of the gas filter.

2. The Relevant Technology

Bioreactors are used in the growth of cells and microorganisms. A typical bioreactor includes a container which holds a culture comprised of liquid growth media, cells or microorganisms, and other desired nutrients and components. A rotatable impeller is operated within the culture to maintain the culture in a substantially homogenous state. Small gas bubbles are continuously sparged into the culture and are typically used to help oxygenate the culture, strip out unwanted $CO_2$ from the culture and control the pH of the culture.

To maintain the viability of the cells/microorganisms, the compartment in which the culture is being grown must remain sterile. To remove the sparged gas that is being continuously added to the culture while maintaining sterility of the compartment, the gas is typically exhausted to the environment through a gas filter system. One conventional gas filter system is referred to as a cartridge filter system and includes a rigid, metal housing into which a cartridge filter is removably positioned. Gas from the container is delivered to an inlet on the housing. The gas then travels through the filter within the housing and is then expelled to the environment through an outlet on the housing. The filter prevents any biological matter within the container from being expelled into the environment and prevents any contaminates in the environment from entering into the container. Capsule filters are also used with bioreactors. A capsule filter comprises a rigid plastic housing that permanently encases a filter. Again, the gas is passed through the capsule filter and then expelled to the environment. Capsule filters have a benefit in that they are disposable and thus do not need to be cleaned or sterilized after use.

Although conventional cartridge filter systems and capsule filters used on bioreactors are useful, they have a number of shortcomings. For example, conventional cartridge filter systems and capsule filters typically have a relatively small inlet port and outlet port through which the gas passes. As such, to obtain desired gas flow rates through the filter systems, it can be necessary to operate the system at an elevated gas pressure. Many current bioreactors, however, comprise a flexible bag in which the culture is grown. Such flexible bags cannot operate at elevated gas pressures or they will rupture. To enable operating at a low gas pressure but at a high gas flow rate, some bioreactors use multiple gas filters in parallel to filter the gas. However, gas filters are very expensive and the required use of multiple filters on a single bioreactor is a significant cost to the system.

Accordingly, what is needed in the art is gas filtering systems that can be used with bioreactors that help optimize the use of gas filters to reduce costs. In some embodiments, it would also be advantageous to have such gas filtering systems that enable operating at relatively low gas pressures.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
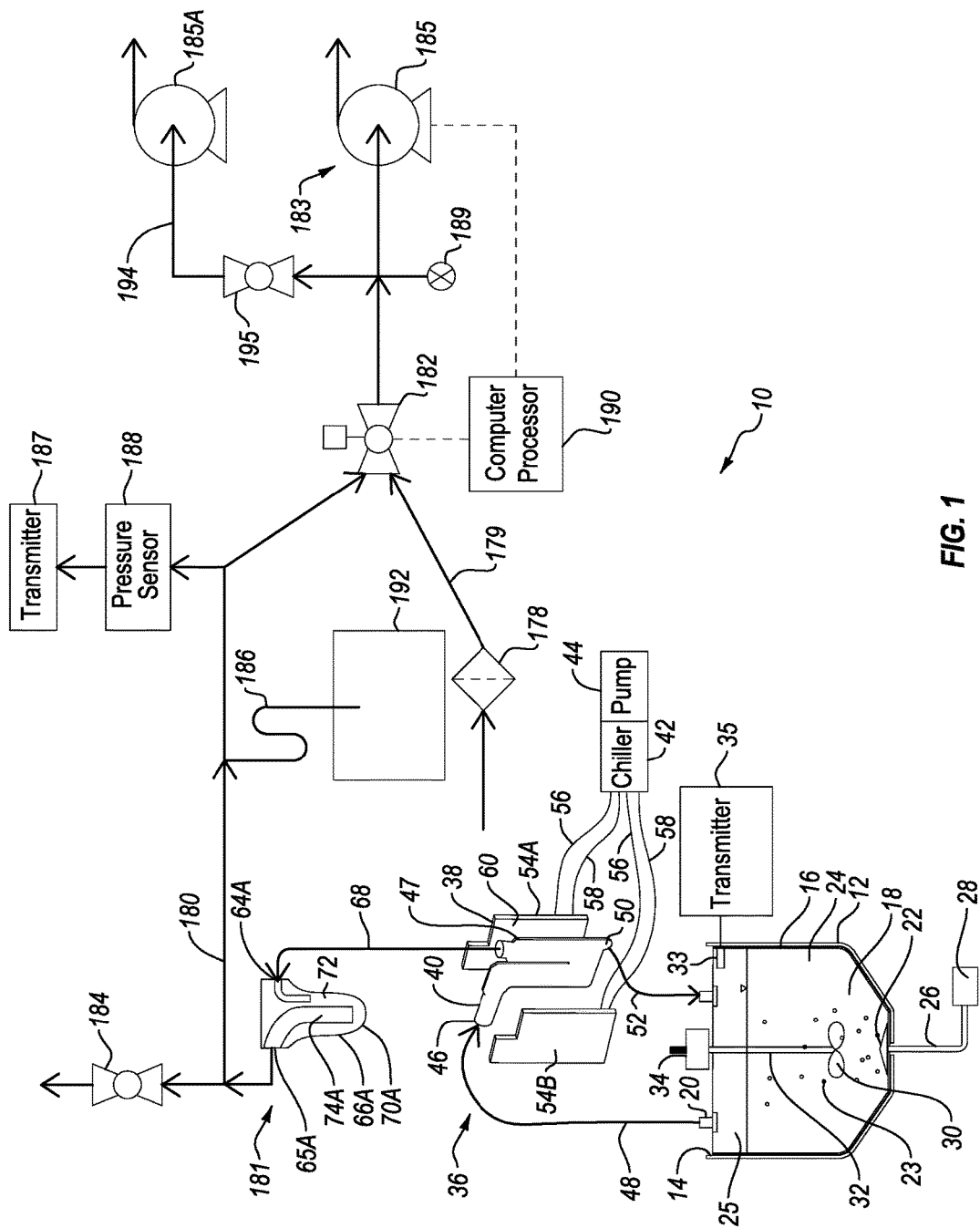
FIG. 1 is a schematic view of one embodiment of an inventive fluid processing system.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present invention, and is not intended to limit the scope of the invention in any manner.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "port" includes one, two, or more ports.

As used in the specification and appended claims, directional terms, such as "top," "bottom," "left," "right," "up,"

"down," "upper," "lower," "proximal," "distal" and the like are used herein solely to indicate relative directions and are not otherwise intended to limit the scope of the invention or claims.

Where possible, like numbering of elements have been used in various figures. Furthermore, multiple instances of an element and or sub-elements of a parent element may each include separate letters appended to the element number. For example two instances of a particular element "91" may be labeled as "91*a*" and "91*b*". In that case, the element label may be used without an appended letter (e.g., "91") to generally refer to instances of the element or any one of the elements. Element labels including an appended letter (e.g., "91*a*") can be used to refer to a specific instance of the element or to distinguish or draw attention to multiple uses of the element. Furthermore, an element label with an appended letter can be used to designate an alternative design, structure, function, implementation, and/or embodiment of an element or feature without an appended letter. Likewise, an element label with an appended letter can be used to indicate a sub-element of a parent element. For instance, an element "12" can comprise sub-elements "12*a*" and "12*b*."

Various aspects of the present devices and systems may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present. Furthermore, as used herein, the terms "connection," "connected," and the like do not necessarily imply direct contact between the two or more elements.

Various aspects of the present devices, systems, and methods may be illustrated with reference to one or more examplary embodiments. As used herein, the term "examplary" means "serving as an example, instance, or illustration," and should not necessarily be construed as preferred or advantageous over other embodiments disclosed herein.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

The present invention relates to fluid processing systems where a fluid, such as a solution and/or suspension, is sparged with a gas and a resulting exhaust gas must subsequently be filtered. The present invention also relates to filter systems that can be used as part of the fluid processing systems and methods for using the forgoing systems. The fluid processing systems can comprise bioreactors or fermenters used for culturing cells or microorganisms. By way of example and not by limitation, the inventive systems can be used in culturing bacteria, fungi, algae, plant cells, animal cells, protozoans, nematodes, and the like. The inventive systems can accommodate cells and microorganisms that are aerobic or anaerobic and are adherent or non-adherent. The systems can also be used in association with the formation and/or treatment of solutions and/or suspensions that are not biological but nevertheless incorporate sparging and gas filtration. For example, the systems can be used in the production of media, chemicals, food products, medicines, beverages, and other liquid products that require sparging with a gas.

The inventive systems can be designed so that a majority of the system components that contact the material being processed are disposed of after a single use. As a result, the inventive systems substantially eliminate the burden of cleaning and sterilization required by conventional stainless steel mixing and processing systems. This feature also ensures that sterility can be consistently maintained during repeated processing of multiple batches. In view of the foregoing, and the fact that the inventive systems are easily scalable, relatively low cost, and easily operated, the inventive systems can be used in a variety of industrial and research facilities that previously outsourced such processing.

Depicted in FIG. 1 is one examplary embodiment of an inventive fluid processing system 10 incorporating features of the present invention. Fluid processing system 10 comprises a rigid support housing 12 bounding a chamber 14. Support housing 12 can be scaled to any desired size. For example, it is envisioned that support housing 12 can be sized so that chamber 14 can hold a volume of less than 50 liters, more than 5,000 liters, or a volume therebetween. Support housing 12 is typically made of metal, such as stainless steel, but can also be made of other materials capable of withstanding the applied loads of the present invention. Where needed, support housing 12 can be jacketed to permit heated or cooled fluid to be pumped therethrough for regulating the temperature of the fluid housed within chamber 14 of support housing 12, as discussed below.

Disposed within support housing 12 is a container 16 that bounds a compartment 18. In one examplary embodiment, container 16 comprises a flexible bag. Container 16 can be comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

In one embodiment, container 16 comprises a two-dimensional pillow style bag wherein two sheets of material are placed in overlapping relation and the two sheets are bounded together at their peripheries to form compartment 18. Alternatively, a single sheet of material can be folded over and seamed around the periphery to form the internal compartment. In another embodiment, container 16 can be formed from a continuous tubular extrusion of polymeric material that is cut to length and is seamed closed at the ends. In still other embodiments, container 16 can comprise a three-dimensional bag that not only has an annular side wall but also a two dimensional top end wall and a two dimensional bottom end wall.

It is appreciated that container 16 can be manufactured to have virtually any desired size, shape, and configuration. For example, container 16 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although in the above discussed embodiment container 16 has a flexible, bag-like configuration, in alternative embodiments it is appreciated that container 16 can comprise any form of collapsible container or semi-rigid container. In some embodiments, container 16 can comprise a rigid container, such as comprised of metal, molded plastic or a composite. In this embodiment, support housing 12 can be eliminated as container 16 is self-supporting.

Ports 20 can be coupled to container 16 so as to communicate with compartment 18. Any desired number of ports 20 can be used and they can be positioned at any location on container 16. Ports 20 can be the same configuration or different configurations and can be used for a variety of different purposes. For example, ports 20 can be coupled with fluid lines for delivering media, cell cultures, and/or other components into and out of container 16. Ports 20 can also be used for coupling probes to container 16. For example, when container 16 is used as a bioreactor for growing cells or microorganisms, ports 20 can be used for coupling probes and sensors such as temperature probes, pH probes, dissolved oxygen probes, pressure sensors and the like. Examples of ports 20 and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 20 can also be used for coupling container 16 to secondary containers and to other desired fittings.

In one embodiment of the present invention, means are provided for delivering a gas into the lower end of container 16. By way of example and not by limitation a sparger 22 can be either positioned on or mounted to a lower end of container 16 for delivering a gas to a fluid 24 disposed within container 16. In the present embodiment, fluid 24 comprises a culture that includes cells or microorganisms. In other embodiments, however, fluid 24 can comprise other solutions, suspension, or liquids as discussed herein. As is understood by those skilled in the art, various gases are typically required in the growth of cells or microorganisms within container 16. The gas typically comprises air that is selectively combined with oxygen, carbon dioxide and/or nitrogen. However, other gases can also be used. The addition of these gases can be used to regulate the dissolved oxygen and $CO_2$ content and to regulate the pH of a culture solution. Depending on the application, sparging with gas can also have other applications. A gas line 26 extends from a gas source 28 to sparger 22 for delivering the desired gas to sparger 22.

Sparger 22 can have a variety of different configurations. For example, sparger 22 can comprise a permeable membrane or a fritted structure comprised of metal, plastic or other materials that dispense the gas in small bubbles into container 16. Smaller bubbles can permit better absorption of the gas into the fluid. In other embodiments, sparger 22 can simply comprise a tube, port, or other type opening formed on or coupled with container 16 through which gas is passed into compartment 18. Examples of spargers and how they can be used in the present invention are disclosed in United States Patent Publication Nos. 2006-0270036 and 2006-0240546 which are incorporated by reference. Other conventional spargers can also be used.

In one embodiment of the present invention, means are provided for mixing fluid 24 contained within container 16. By way of example and not by limitation, an impeller 30 or other mixing element is disposed within compartment 18. Impeller 30 is rotated by a drive shaft that projects into container 16 through a dynamic seal 34. External rotation of drive shaft 32 thus facilitates rotation of impeller 30 which mixes fluid 24 within container 16.

In another embodiment, drive shaft 32 can project into container 16 through a flexible tube having one end rotatably connected to container 16 and an opposing second end connected to impeller 30. Drive shaft 32 passes through the flexible tube and removably couples with impeller 30 so that drive shaft 32 can rotate impeller 30 without directly contacting fluid 24. Examples of this mixing system are disclosed in U.S. Pat. No. 7,384,783, issued Jun. 10, 2008 and U.S. Pat. No. 7,682,067, issued Mar. 23, 2010 which are incorporated herein by specific reference. In another alternative embodiment, drive shaft 32 can be configured to repeatedly rise and lower a mixing element located within container 16 for mixing the fluid. Alternatively, a magnetic stir bar or impeller can be disposed within compartment 18 of container 16 and rotated by a magnetic mixer disposed outside of container 16. In yet other embodiments, a stir bar, paddle, or the like that projects into compartment 18 of container 16 can be pivoted, swirled, shook or otherwise moved to mix fluid 24. In addition, the mixing can be accomplished by circulating fluid through compartment 18, such as by using a peristaltic pump to move the fluid into and out of compartment 18 through a tube having opposing ends sealed to container 16. Gas bubbles can also be passed through the fluid to achieve the desired mixing. Finally, support housing 12 and container 16 can be pivoted, rocked, rotated or otherwise moved so as to mix fluid 24 within container 16. Other conventional mixing techniques can also be used. Specific examples of how to incorporate a mixer into a flexible bag, such as container 16, are disclosed in U.S. Pat. No. 7,384,783, issued Jun. 10, 2008; U.S. Pat. No. 7,682,067, issued Mar. 23, 2010; and US Patent Publication No. 2006/0196501, issued Sep. 7, 2006 which are incorporated herein by specific reference.

Coupled with container 16 is a pressure sensor 33 that is used to sense the gas pressure within compartment 18. Specifically, during use a head space 25 is formed above fluid 24. Pressure sensor 33 is positioned so as to be disposed within or otherwise communicate with head space 25 so as to sense the pressure therein. It is appreciated that any conventional pressure sensor can be used. Pressure sensor 33 can be coupled with a transmitter 35 for transmitting readings from pressure sensor 33 to a computer processor 190. Alternatively, pressure sensor 33 can be wired to computer processor 190. The operation of pressure sensor 33 and computer processor 190 will be discussed below in greater detail.

Although not required, in one embodiment of the present invention a condenser system 36 is coupled with container 16 for condensing the moisture that escapes from container 16 with the exhaust gas. In general, condenser system 36 comprises a condenser 38, a condenser bag 40, a chiller 42, and a pump 44. More specifically, condenser bag 40 comprises a two or three dimensional flexible bag made from one or more sheets of polymeric film, such as the materials discussed above with regard to container 16. Condenser bag 40 has an inlet end 46 and an opposing outlet end 47. Inlet end 46 is fluid coupled with compartment 18 of container 16 such as by being directly coupled to an upper end of container 16 or, as depicted, by a gas line 48 extending from the upper end of container 16 to inlet end 46. Gas line 48, as with all of the other gas lines and fluid lines discussed herein, can comprise flexible tubing, a tube comprised of film, a rigid conduit or other conduits. Formed between inlet end 46 and outlet end 47 of condenser bag 40 is a catch 50, typically having a U-shaped configuration. As discussed below, moisture condensed within condenser bag 40 collects at catch 50.

A fluid line 52 has a first end coupled with catch 50 and an opposing second end coupled with either container 16 or a separate fluid reservoir. As such, fluid line 52 can be used to either return the condensed moisture back to container 16 or to collect the condensed moisture within the fluid reservoir for subsequent use or disposal. Depending on the position and configuration of condenser bag 40, the condensed moisture can either freely flow through fluid line 52 under the force of gravity or can be pumped through fluid line 52 such as by attaching a peristaltic pump to fluid line 52. In another alternative embodiment, the second end of fluid line 52 can be coupled with gas line 48 or to inlet end 46 of condenser bag 40 so that the fluid delivered there will then flow down into container 16.

Condenser 38 comprises a pair of panels 54A and 54B that each bound a fluid path that extends therethrough. Each panel 54 has an inlet communicating with the fluid path and coupled with a fluid line 56 and an outlet communicating with the fluid path and coupled with a fluid line 58. The opposing ends of fluid lines 56 and 58 communicate with chiller 42. Specifically, a fluid is chilled by chiller 42 and then pumped by pump 44 through fluid line 56, through the fluid path within panel 54 and then back to chiller 42 through fluid line 58 where the process is then repeated. Panels 54 are typically comprised of a metal, such as aluminum, or some other high thermally conductive material. As such, passing the chilled fluid through panels 54 causes panels 54 to cool. Panels 54 typically have a substantially flat inside face 60 that is disposed directly against opposing side faces of condenser bag 40. Accordingly, as humid gas is passed through condenser bag 40, the humid gas is cooled by heat transfer with panels 54 such that the moisture within the humid gas condenses into a liquid that collects at catch 50, as discussed above. Specific examples of each of the components of condenser system 36, how condenser bag 40 can fluid couple with container 16, how the liquid from the condensed moisture can be returned to container 16 and alternative embodiments of condenser systems that can be used in the present invention are disclosed in U.S. Pat. No. 8,455,242, issued Jun. 4, 2014 and US Patent Publication No. 2015/0265943, published Sep. 24, 2015, which are incorporated herein by specific reference. Other conventional condenser systems can also be used.

In alternative embodiments, it is appreciated that condenser system 36 can comprise any conventional condenser system that can be used to condense moisture from a gas. Such conventional systems typically do not include a condenser bag 40 but often have rigid or semi-rigid conduits through which the gas passes and which are located within or directly adjacent to a cooling source.

In view of the foregoing, during use fluid 24 is dispensed into compartment 18 of container 16. As previously discussed, fluid 24 can comprise a culture of cells or microorganisms along with media, nutrients, and other desired components or, alternatively, other types of fluids that require processing. Where the fluid must remain sterile, container 16, and specifically compartment 18 thereof, is sterilized, such as by radiation, prior to use. Gas bubbles 23 are sparged into fluid 24 through sparger 22. Concurrently, impeller 30 or some other mixing element is operated so as to mix fluid 24 and typically maintain it substantially homogenous. Gas bubbles 23 pass through fluid 24 making a mass transfer therewith and then collect within head space 25 located at an upper end of container 16. As the gas pressure increases, the sparged gas which is humid travels into condenser bag 40 through gas line 48. Moisture within the humid gas is condensed by condenser 36 and returned to container 16 or delivered to some other fluid reservoir as previously discussed.

The now dehumidified gas passes out of outlet end 47 of condenser bag 40 and travels to an intake port 64A of a filter assembly 66A. Condenser bag 40 can be directly coupled to filter assembly 66A, such as by directly coupling together ports located on condenser bag 40 and filter assembly 66A, or can be fluid coupled together by a gas line 68 extending therebetween, as depicted. In other embodiments, condenser system 36 can be eliminated so that filter assembly 66A couples with container 16 either directly or through a gas line.

In one examplary embodiment, filter assembly 66A comprises a casing 70A that bounds a compartment 72. Disposed within compartment 72 is a filter 74A. The gas from gas line 68 enters compartment 72 through intake port 64A, passes through filter 74A and then exits through an exhaust port 65A. As such, all of the gas passing through filter assembly 66A passes through filter 74A. In one embodiment, filter 74A can comprise a cartridge filter while casing 70A comprises a rigid housing, such as a metal housing, in which the cartridge filter can be removably received. In an alternative embodiment, filter assembly 66A can comprise a capsule filter wherein filter 74A is permanently enclosed within a rigid outer casing, such as a polymeric casing.

Filter 74A is typically made of a porous material through which gas can pass but through which unwanted contaminants, such as bacteria and microorganisms, cannot. The porous material is typically hydrophobic which helps it to repel liquids. For example, filter 74A can be comprised of polyvinylidene fluoride (PVDF). Other materials can also be used. Where the system is acting as a bioreactor or fermentor, filter 74A typically needs to operate as a sterilizing filter and will thus typically have a pore size of 0.22 micometers ($\mu m$) or smaller. The term "pore size" is defined as the largest pore in the material through which a particle can pass. Commonly, filter 74A has a pore size in a range between 0.22 and 0.18 $\mu m$. However, for pre-filtering applications or for non-sterile applications, filter 74A can have a larger pore size, such as in a range between about 0.3 and 1.0 $\mu m$. In still other applications, the pore size can be greater than 1.0 $\mu m$. One example of filter 74A is the DURAPORE 0.22 $\mu m$ hydrophobic cartridge filter produced by Millipore. Another example is the PUREFLO UE cartridge filter available from ZenPure.

Figure 2:
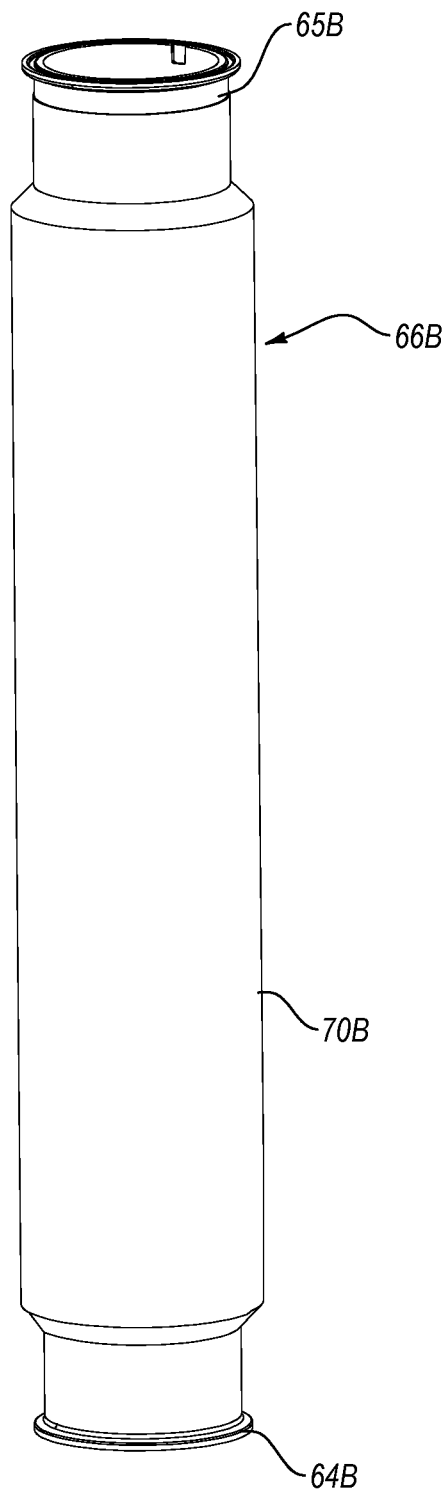
FIG. 2 is a perspective view of an alternative embodiment of a gas filter system that can be used in the fluid processing system depicted in FIG. 1.

Depicted in FIG. 2 is a filter assembly 66B which is an alternative embodiment of and can be used in place of filter assembly 66A. Filter assembly 66B comprises a casing 70B having an intake port 64B mounted at one end and an exhaust port 65B mounted on an opposing end. Casing 70B comprises a flexible, collapsible bag comprised of one or more sheets of polymeric material such as polymeric film. Casing 70B can be comprised of the same materials and be produced using the same manufacturing methods as previously discussed above with regard to container 16. In the depicted embodiment, casing 70B comprises a pillow type bag that is manufactured from two overlapping sheets of polymeric film that are seamed together along perimeter edges. In some applications, filter assembly 66, condenser bag 40, container 16 and the gas lines that extend therebetween can all be sterilized prior to use.

Figure 3:
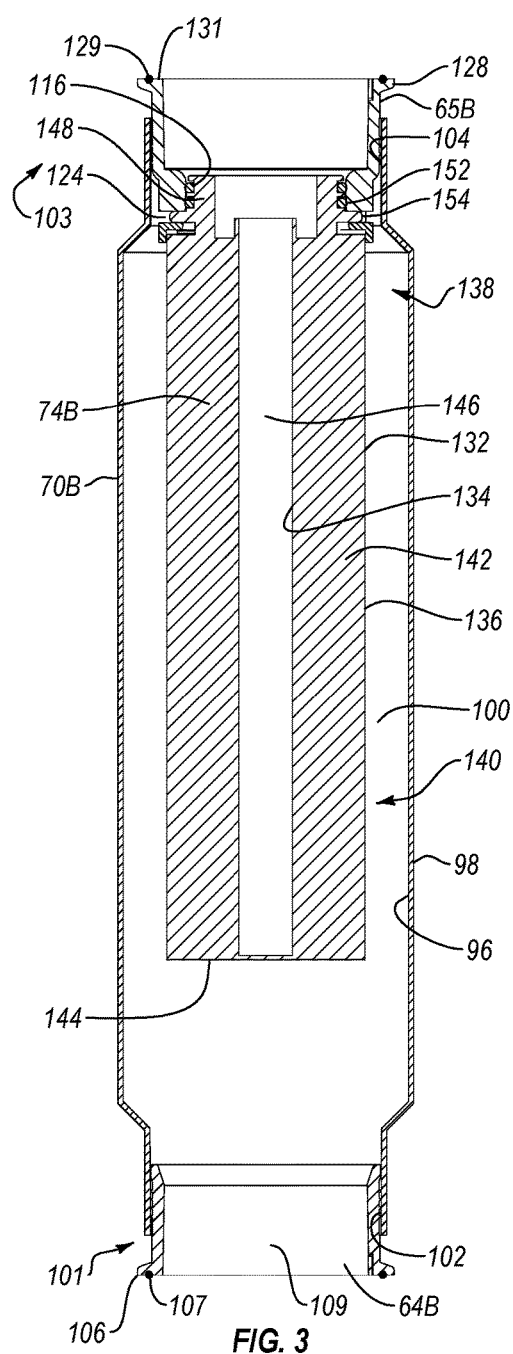
FIG. 3 is a cross sectional side view of the gas filter system depicted in FIG. 2.

As depicted in FIG. 3, casing 70B has an interior surface 96 and an opposing exterior surface 98. Interior surface 96 bounds a compartment 100. Casing 70B has a first end 101 at which an inlet opening 102 is formed. Inlet opening 102 is configured to be coupled with intake port 64B. Casing 70B also has an opposing second end 103 at which an outlet opening 104 is formed. Outlet opening 104 is configured to be coupled with exhaust port 65B.

Figure 4:
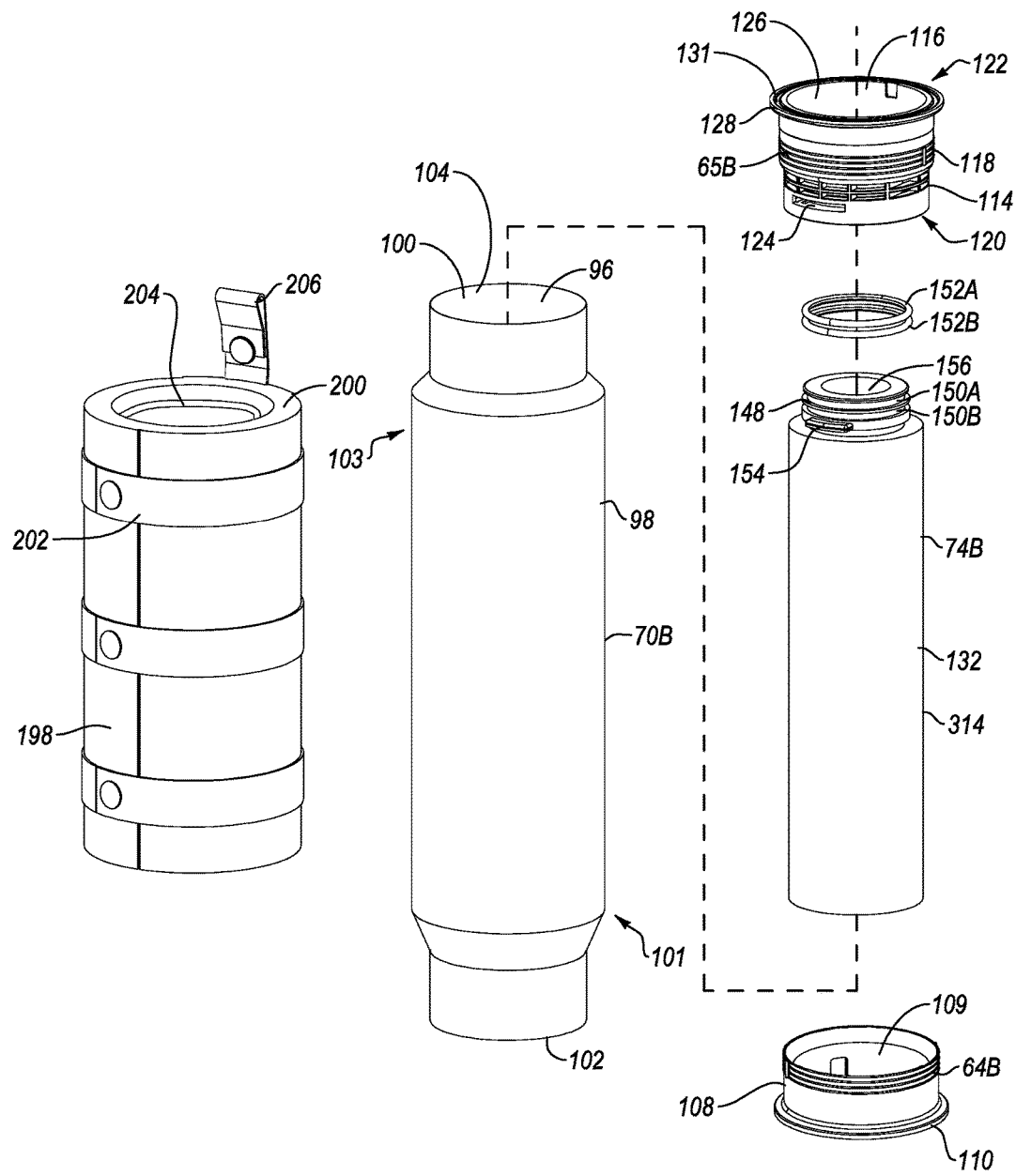
FIG. 4 is a partially exploded view of the gas filter system depicted in FIG. 2.

As depicted in FIG. 4, intake port 64B comprises a tubular stem 108 that bounds a port opening 109 extending therethrough. An annular coupling flange 110 encircles and radially, outwardly projects from stem 108. Coupling flange 110 has an end face 106 (FIG. 3) with an annular seal 107, such as an O-ring, disposed thereon. Stem 108 of intake port 64B can be secured to casing 70B by being received within inlet opening 102 and welded to casing 70B so that coupling flange 110 is openly exposed. Port opening 109 thus communicates with compartment 100 of casing 70B. A port identical to intake port 64B can be mounted at outlet end 47 of condenser bag 40. A sealed coupling between condenser bag 40 and filter assembly 66B can then be achieved by simply clamping the coupling flanges together, such as through the use of a tri-clamp.

Continuing with FIG. 4, exhaust port 65B comprises a tubular stem 114 having an interior surface 116 and an opposing exterior surface 118 extending between a first end 120 and an opposing second end 122. Formed on interior surface 116 at first end 120 is a connector. In the depicted embodiment, the connector comprises a pair of opposing bayonet slots 124 (FIG. 3) formed on first end 120 so as to form half of a bayonet connection. Interior surface 116 bounds a port opening 126 extending through exhaust port 65B and which can have the same configurations and dimensions as port opening 109 of intake port 64B. Encircling and radially outwardly projecting from second end 122 of stem 114 is a coupling flange 128. An annular seal 129 is formed on an end face 131 thereof. During attachment, first end 120 of stem 114 of exhaust port 65B can be received within outlet opening 104 and welded to casing 70B so that flange 128 is openly exposed.

Disposed within casing 70B is a filter 74B that is coupled with exhaust port 65B. As depicted in FIGS. 3 and 4, filter 74B comprises a filter body 132 having an interior surface 134 and an exterior surface 136 extending between a first end 138 and an opposing second end 140. Filter body 132 includes a tubular side wall 142 that extends between opposing ends 138 and 140 and a floor 144 disposed at second end 140. As such, interior surface 134 bounds a blind channel 146 that centrally extends along the length of filter body 132 but which is blocked at second end 140 by floor 144. Upwardly projecting from first end 138 of filter body 132 is a tubular neck 148. A pair of annular grooves 150A and B encircle the exterior surface of neck 148 and are configured to receive corresponding annular seals 152A and B. Also outwardly projecting from the exterior surface of neck 148 at a location below grooves 150A and B are a pair of opposing bayonet prongs 154. An opening 156 extends through neck 148 and communicates with channel 146. Filter body 132 can be made from the same materials and have the same properties, including pore size, as discussed above with regard to filter 74A.

During assembly, seals 152 are received within annular grooves 150 following which neck 148 of filter 74B is coupled to exhaust port 65B by bayonet prongs 154 being received and rotated within bayonet slots 124. In this configuration, filter 74B is securely attached to exhaust port 65B with seals 152 forming a gas tight seal between neck 148 and interior surface 116 of exhaust port 65B. Next, filter 74B is slid within casing 70B so that exhaust port 65B is partially received within casing 70B. A gas tight seal is then formed between casing 70B and exhaust port 65B such as by welding casing 70B to exterior surface 118 of stem 114.

During use, as discussed below in more detail, gas from condenser bag 40 or directly from container 16 enters filter assembly 66B at intake port 64B but can only exit filter assembly 66B by passing through filter body 132, traveling along channel 146 and then exiting out through exhaust port 65B. As such, filter 74B sterilizes or otherwise filters all gas passing out of filter assembly 66B. Filter 74B also functions as a sterilizing filter that prevent outside contaminates from accessing the compartment of filter assembly 66B which could then potentially contact the fluid 24 within container 16.

Filter assembly 66B is designed to be capable of filtering high flow rates of gas. Specifically, as gas enters filter assembly 66B, flexible casing 70B expands to the configuration shown in FIG. 3. In the expanded configuration, casing 70B is spaced apart from exterior surface 136 of filter body 132 along the length of filter body 132. As such, the gas can freely access and pass through filter body 132 from all sides and along the full length of filter body 132, thereby optimizing the use of filter body 132 and maximizing the gas flow rate therethrough. In one embodiment, the annular gap distance D between exterior surface 136 of filter body 132 and the interior surface of casing 70B is in a range between about 0.15 cm to about 3 cm with between about 0.2 cm to about 1 cm being more common. In some embodiments, the gap distance D can be greater than 1 cm or 2 cm. Other dimensions can also be used. In one embodiment filter body 132 has a maximum transverse diameter in a range between about 5 cm and about 10 cm. Other dimensions can also be used. Furthermore, gap distance D typically extends over at least 80% and more commonly at least 90%, 95% or 100% of the length of filter body 132. Filter assembly 66B can also process a high gas flow rate because the port openings of intake port 64B and exhaust port 65B can be designed having a surprising large diameter, such as greater than 3 cm, 4 cm, 5 cm or 6 cm. In addition, as discussed below, filter assembly 66B can be designed to simultaneously operate with a plurality of filters 74B that are disposed in parallel communication with the gas flow.

The inventive fluid processing system 10, depending on the size thereof, can commonly operate at gas flow rates greater than 200 or 600 standard liters per minute ("slpm") and depending on the size thereof, it is envisioned that it can operate at gas flow rates greater than 2000, 5,000 or 10,000 slpm. Of course, the system can also operate at lower flow rates. Expressed in other terms, some embodiments of the system commonly operate at a gas flow rate between about 0.001 to about 2.5 vessel volumes per minute (based on the volume of container 16) with about 0.1 to about 1.0 vessel volumes per minute being more common. Other flow rates can also be used.

Figure 3A:
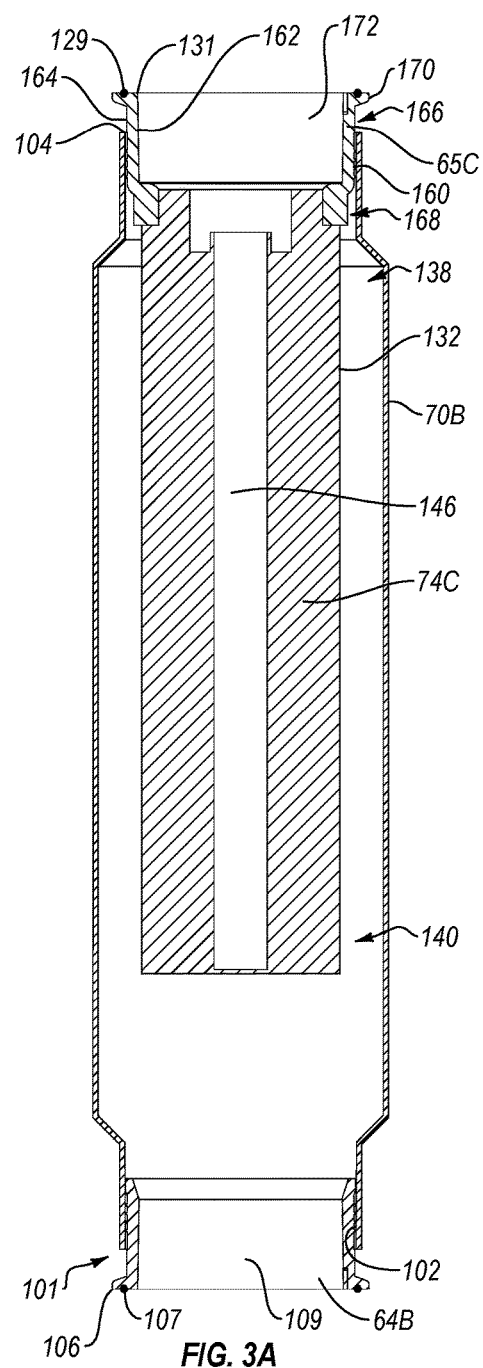
FIG. 3A is a cross sectional side view of an alternative embodiment of the gas filter system depicted in FIG. 3.

In one alternative embodiment, the filter and exhaust port can be formed as a single piece. For example, depicted in FIG. 3A is a filter 74C. Like elements between filter 74C and previously discussed filter 74B are identified by like reference characters. Filter 74C includes filter body 132 which has the same structure, composition and properties as previously discussed. However, rather than including neck 148 at first end 138, filter 74C includes an exhaust port 65C that is permanently fixed to first end 138 of filter body 132, such as by over molding, adhesive, welding, or the like. As such, no separate seal is needed between exhaust port 65C and filter body 132.

Exhaust port 65C includes a stem 160 having an interior surface 162 and an opposing exterior surface 164 that extend between a first end 166 and an opposing second end 168. Second end 168 is secured to filter body 132 as discussed above. Encircling and outwardly projecting from first end 166 is a flange 170. Interior surface 162 bounds a port opening 172 that extends therethrough and communicates with channel 146 of filter body 132. Filter body 132 is received within casing 70B and exterior surface 164 of exhaust port 65C is received within outlet opening 104 of casing 70B. Exterior surface 164 is sealed to casing 70B, such as by welding, so as to form a gas tight seal. Exhaust port 164 is typically comprised of a non-porous polymeric material while filter body 132 is comprised of a porous material, as previously discussed.

In another embodiment, it is envisioned that exhaust port 65C could be eliminated and that casing 70B could be welded or otherwise secured directly to first end 138 of filter body 132. Further discussion on filter assembly 66B, alternative embodiments thereto and how filter assembly 66B can be attached to condenser bag 40 and container 16 are disclosed in US Patent Publication No. 2015/0265958, published Sep. 24, 2015, which is incorporated herein by specific reference.

Also depicted in FIG. 4 is a heating jacket 198 that can be disposed on casing 70A (FIG. 2) or casing 70B. Heating Jacket 198 includes an insulation pad 200 that can be wrapped into a cylindrical loop and held in the desired configuration by straps 202 that encircle the exterior of pad 200. Disposed either within pad 200 or on the interior surface thereof is an electrical heating element 204 such as heat tape or the like. A hanger 206 can also project from the upper end of pad 200 by connecting to either pad 200 or straps 202. During use, heating jacket 198 is wrapped around a corresponding casing 70A, 70B. Jacket 198, however, is sized so that casing 70B can still inflate to provide the desired gap between filter 74B and casing 70B but is also typically configured so that casing 70A, 70B push against the interior surface of heating jacket 198 to produce an efficient heat transfer therebetween. Moisture that passes out of condenser system 36 and into filter assembly 66 will collect on filters 74 and eventually clog the filters. By activating electrical heating element 204, heating jacket 198 assists to heat and vaporize the condensed liquid on filters 74 so that it can pass through and out of filters 74, thereby prolonging the active life of filters 74.

Returning to FIG. 1, a transfer line 180 has a first end 181 coupled with exhaust port 65 (i.e., exhaust port 65A or 65B) of filter assembly 66 (i.e., filter assembly 66A or 66B) and an opposing second send 183 coupled with a vacuum pump 185. Transfer line 180 can comprise flexible tubing, a rigid conduit, vacuum hose, or any other type of conduit that can operate under a negative pressure without fully collapsing. During operation, vacuum pump 185 is activated which produces a partial vacuum or negative pressure within transfer line 180. The partial vacuum/negative pressure is applied to exhaust port 65 of filter assembly 66 which functions to help pull the exhaust gas through filter 74. The applied negative pressure is typically less (i.e., more negative) than 0 kPa and more commonly less than −0.5, −1, −5 or −10 kPa. The maximum negative pressure is typically greater (i.e., more positive) than −100 kPa and more commonly greater than −80, −50, −30 or −20 KPa. The applied negative pressure is thus commonly between −0.5 kPa and −80 kPa with between −0.5 kPa and −50 kPa or between −0.5 kPa and −20 kPa being more common. Other values can also be used. Likewise, the pressure differential across filter 74 between intake port 64 and exhaust port 65 is typically in the range between 0.5 kPa and 80 kPa with between 0.5 kPa and 50 kPa or between 0.5 kPa and 20 kPa or between 0.5 kPa and 10 kPa being more common. Again, other values can also be used.

Applying a partial vacuum or negative pressure to exhaust port 65 of filter assembly 66 has been found to achieve a number of benefits. For example, because of the relative small pore size of filter 74, there is a substantial pressure loss as the gas passes through filter 74. This can be problematic, however, where there is a need to sparge gas at a high flow rate through fluid 24. That is, filter 74 restricts the flow of gas through filter assembly 74. To enable the flow of gas passing through filter 74 to keep up with the flow of gas being sparged into fluid 24, one option is to increase the gas pressure on the upstream side of filter 74 so as to more rapidly force the gas through filter 74. However, where casing 70B, condenser bag 40 and/or container 16 are comprised of a polymeric film, they are typically designed to operate at an internal gas pressure under 10 kPA and typically in a range between 0.1 kPa and 8 kPa with between 0.5 kPa and 5 kPa or between 0.5 kPa and 2 kPa being more common. It is noted that that casing 70B, condenser bag 40 and/or container 16 are designed to operate at some positive pressure so that they remain inflated. At gas pressures above 50 kPa or more commonly 60 kPa or 70 kPa, the polymeric film and/or the seams formed therewith can rupture, thereby allowing contamination to enter the sterile environment and eventually contaminate fluid 24. Accordingly, where casing 70, condenser bag 40 and/or container 16 are comprised of a polymeric film or otherwise have a lightweight structure, safe operating conditions can preclude any significant elevation of the gas pressure upstream from filter 74.

Casing 70, condenser bag 40 and container 16 could be formed as rigid structures that safely withstand higher gas pressures. However, in some situations there can be significant benefits in using casing 70, condenser bag 40 and/or container 16 where they are made from a polymeric film. For example, where casing 90, condenser bag 40 and/or container 16 are formed from a polymeric film, they are easier to produce and substantially less expensive than their rigid counterparts, thereby decreasing expense. Furthermore, because casing 70, condenser bag 40 and/or container 16 are relatively inexpensive to produce, they can be disposed of after a single use. As a result, no cleaning or sterilization is required between batches and there is less risk of the process fluid becoming contaminated.

One alternative to increasing the gas pressure upstream of filter 74 is to fluid couple a plurality of filter assemblies 66 in parallel to condenser system 36 so that the filter assemblies 66 can process the gas flow rate at a lower gas pressure. However, the problem with this approach is that filters 74 are very expensive. Thus, although this approach is feasible, it is desirable to minimize the number of filters 74 that are used so as to lower costs.

In contrast to using the above approaches, the benefit of applying a partial vacuum or negative pressure to exhaust port 65 of filter 74 is that the applied negative pressure increases the flow rate of gas through filter 74 and decreases the gas pressure upstream of filter 74. As such, casing 70, condenser bag 40 and/or container 16 can still safely be used in fluid processing system 10 where they are comprised of polymeric film because the system can operate at a lower pressure. Although in some embodiments, as discussed below, it may still be necessary to use a plurality of filters 74 in parallel to accommodate for high flow rates of sparged gas, by applying a partial vacuum/negative pressure to the exhaust port of each filter 74, significantly fewer filters or smaller filters can be required, thereby minimizing costs. An additional benefit of applying a partial vacuum/negative gas pressure to exhaust port 65 of filter 74 is that it extends the productive life over which filter 74 can be used. That is, filter 74 can be used longer when the negative gas pressure is applied to exhaust port 65 of filter 74. By using a filter longer, fewer or smaller filters are required which helps to minimize costs. The above benefits are also achieved independent of the type of filter assembly, condenser system and fluid container used. That is, even if the filter assembly, condenser system and fluid container are formed as a rigid structure that can operate at an elevated gas pressure, applying the negative pressure to the exhaust port of the filter assembly will reduce the number or size of filters that are required.

The partial vacuum/negative pressure applied to exhaust port 65 by vacuum pump 185 is typically maintained at a value so that the gas pressure upstream from filter 74 is positive and within the preferred operating range as previously discussed, i.e., typically between 0.1 kPa and 2 kPa. If the partial vacuum/negative pressure is too great, the gas pressure upstream from filter 74 can be negative or sufficiently low that casing 74B collapses against filter 70B, thereby restricting the flow of gas through filter 70B. Collapsing condenser bag 40 and/or container 16 can also restrict gas flow and negatively affect other operating conditions. Where casing 70, condenser bag 40 and/or container 16 are sufficiently rigid that they can withstand a negative pressure without collapsing, the applied partial vacuum/negative pressure can be increased to produce a negative pressure within one or more of casing 70, condenser bag 40 and container 16.

Vacuum pump 185 can come in a variety of different configurations and be used in a number of different ways to achieve the desired partial vacuum/negative pressures and maintain the desired gas flow rates. Vacuum pump 185 typically comprises a positive displacement pump such as a rotary vane pump or diaphragm pump. However, other types of pumps can also be used.

Vacuum pump 185 can also comprise a variable displacement pump or a fixed displacement pump. Variable displacement pumps can be directly controlled to adjust the partial vacuum they produce. In contrast, fixed displacement pumps only operate to produce a constant partial vacuum. The produced constant partial vacuum, however, can be regulated during application by diverting the vacuum to ambient, e.g., adjusting the delivery of a separate gas into the vacuum line. For example, where vacuum pump 185 is a fixed displacement pump, a three-way control valve 182 can be coupled with transfer line 180. An air particle filter 178 is coupled with control valve 182 by way of a transfer line 179. As a result, air from the surrounding environment can pass through air particle filter 178, through transfer line 179 and then into transfer line 180 by passing through control valve 182. Thus, although vacuum pump 185 may be producing a constant partial vacuum, by using control valve 182 to regulate the amount of air from the environment that enters transfer line 180 through transfer line 179, the partial vacuum or negative pressure applied to exhaust port 65 of filter 74 can be regulated. In contrast, where vacuum pump 185 is a variable displacement pump, control valve 182, transfer line 179 and air particle filter 178 can be eliminated and the amount of partial vacuum produced by vacuum pump 185 can be regulated by directly controlling the operation of vacuum pump 185.

In one embodiment, the amount of vacuum applied to exhaust port 65 of filter 74 can be manually regulated by inspecting a pressure gauge 189 that is coupled with transfer line 180. That is, based on the reading of pressure gauge 189, an operator can adjust the operation of vacuum pump 185 or, where applicable, adjust control valve 182 so as to adjust the applied partial vacuum.

In one alternative automated embodiment, vacuum pump 185, pressure gauge 189 and/or control valve 182 can be electrically coupled with computer processor 190 which, as previously discussed, is also electrically coupled with pressure sensor 33 that detects the gas pressure within container 16. In this embodiment, computer processor 190 can automatically adjust the applied partial vacuum based on inputs received from pressure gauge 189 and pressure sensor 33. For example, as fluid processing system 10 operates, filter 74 slowly starts to plug which increases the gas pressure upstream from filter 74. Furthermore, the gas pressure upstream from filter 74 can increase by increasing the flow rate of gas sparged into container 16. The gas pressure upstream from filter 74 can also vary as a result of start-up, shut-down and changes in operating conditions.

Computer processors 190 can be programmed to monitor the pressure detected by pressure sensor 33 and to automatically adjust the operation of vacuum pump 185 and/or control valve 182 so that the gas pressure within container 16, condenser bag 40 and/or casing 70 is maintained within the desired operating range. That is, as the pressure increases within container 16, vacuum pump 185 can be adjusted to produce a higher vacuum or control valve 182 can be adjusted to restrict the flow of air into transfer line 180 and thereby also produce a higher vacuum. In turn, increasing the partial vacuum applied to exhaust port 65 of filter 74 increases the gas flow rate through filter 74 and thus lowers the gas pressure within container 16. It is appreciated that the gas pressure detected by pressure sensor 33 attached to container 16 is also approximately the gas pressure within condenser bag 40 and casing 70. As such, pressure sensor 33 can also be located at any position in the gas stream between the compartment of casing 70 (FIG. 3) and headspace 25 of container 16.

As also depicted in FIG. 1, a second vacuum pump 185A can coupled to transfer line 180 by a secondary line 194. Where needed, the applied vacuum can be increased by opening a valve 195 on secondary line 194 and activating second vacuum pump 185A. As needed, additional vacuum pumps can similarly be attached to transfer line 180 either for capacity or redundancy. Valve 195 and second vacuum pump 185A can be electrically coupled with computer processor 190 for automated operation.

Figure 5:
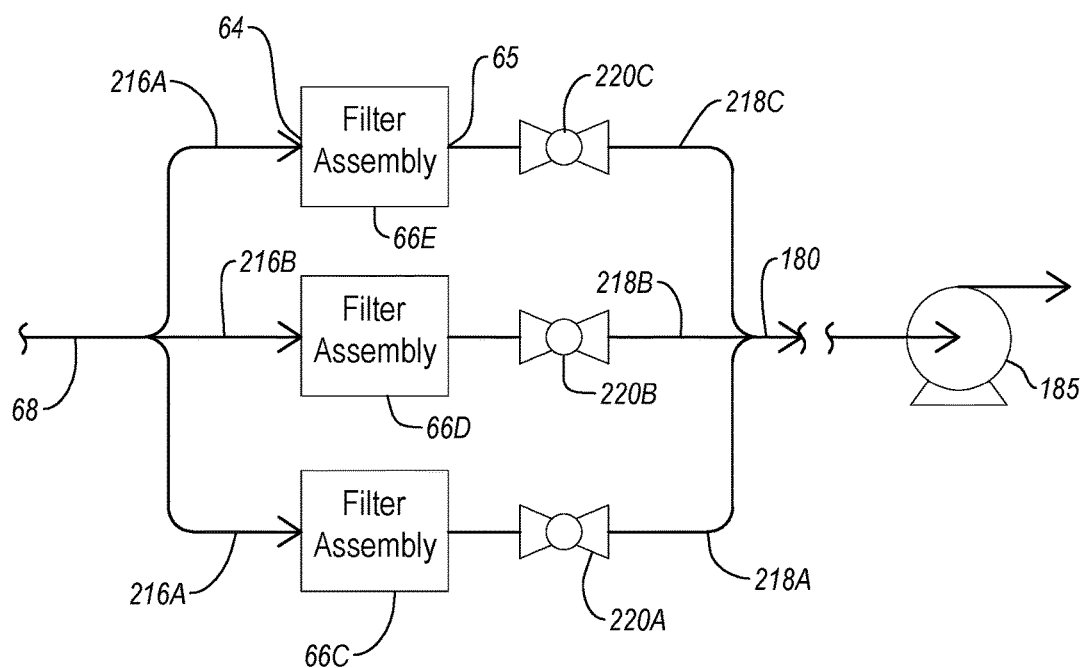
FIG. 5 is a schematic view of a plurality of gas filter systems that can be used with the fluid processing system depicted in FIG. 1.

As previously mentioned, a single filter 74 may not be capable of processing all of the sparged gas while maintaining the pressure upstream of filter 74 within the desired range, even when the partial vacuum is applied to filter 74. This can in part be due to the fact that filter 74 progressively clogs during the fluid processing. Accordingly, a plurality of filters 74 can be fluid coupled in parallel to vacuum pump 185. Specifically, depicted in FIG. 5 are filter assemblies 66C, 66D and 66E which can each be the same as filter assembly 66A or 66B, as previously discussed herein. In any embodiment, each filter assembly 66C-D includes a separate filter 74 within a casing 70. In other embodiments, other numbers of filter assemblies 66 can be used in parallel such as 2, 4, 5, or more. Each filter assembly 66C-D has an intake port 64 that couples with a corresponding tubular gas line section 216A-C, respectively. In turn, each gas line section 216A-C fluid couples with gas line 68. Gas line 68 can couple with condenser system 36 or can directly couple with container 16. Each filter assembly 66C-D also has an exhaust port 65 that couples with a corresponding tubular gas line section 218A-C, respectively. In turn, each gas line section 218A-C fluid couples with transfer line 180. During use, two or more of filter assembly 66C-D can operate concurrently for filtering gas from container 16 and receiving a partial vacuum/negative pressure from vacuum pump 185. Alternatively, valves 220A-C can be coupled with gas line sections 218A-C, respectively, and electrically coupled with computer processor 190. The fluid processing system can initially operate with gas only passing through one or more of filter assembly 66C-D. However, as that filter or filters become plugged and the pressure increases within container 16, subsequent valves 220 can be opened by computer processor 190 so that the gas pressure upstream from filter assembly 66C-D is maintained within desired operating range.

Figure 6:
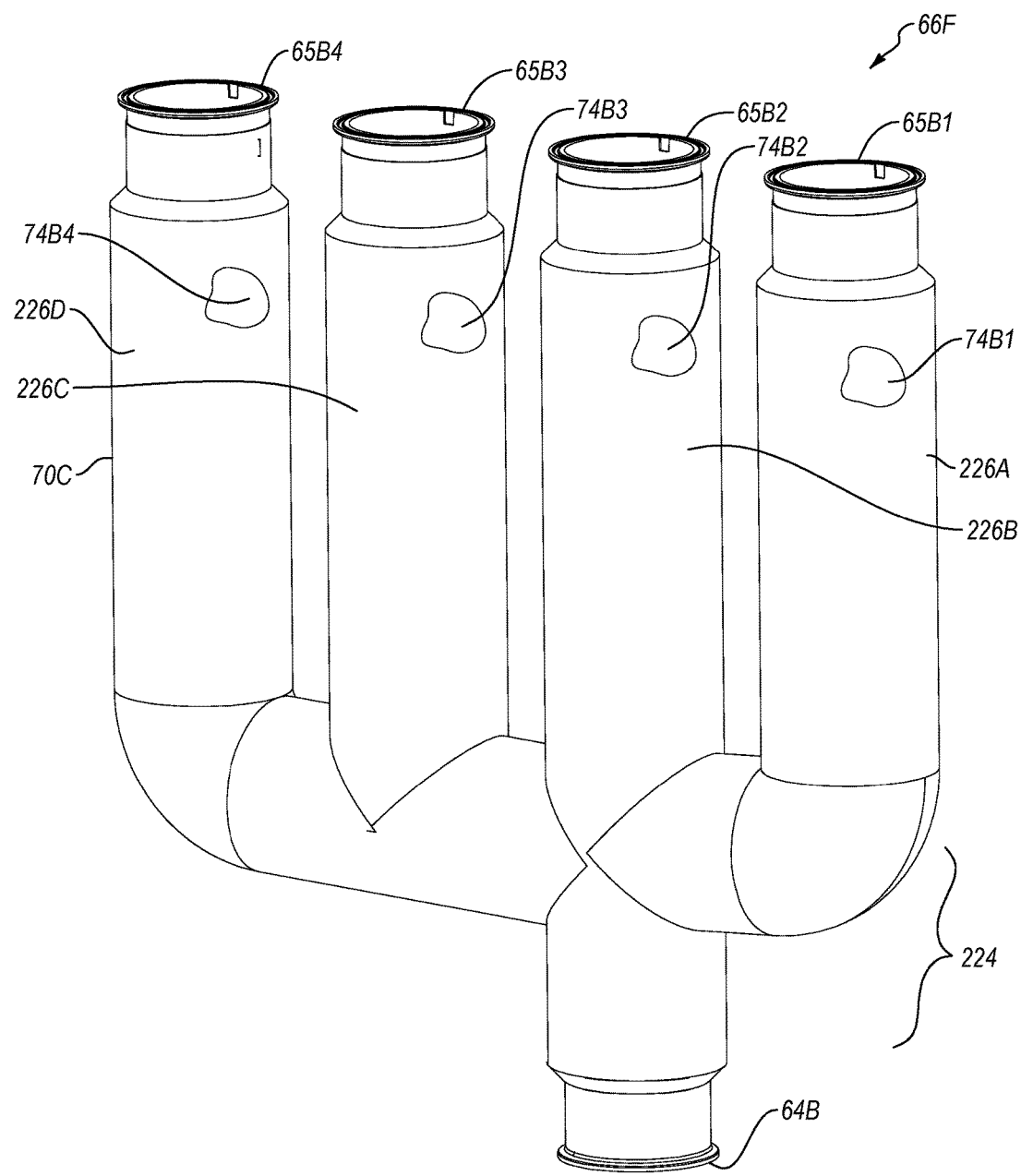
FIG. 6 is a perspective view of an alternative embodiment of a gas filter system that can be used with the fluid processing system depicted in FIG. 1.

Depicted in FIG. 6 is another alternative embodiment of a filter assembly 66F. Like elements between filter assembly 66F and 66B are identified by like reference characters. Filter assembly 66F includes a casing 70C that comprises a manifold section 224 and four spaced apart sleeves 226A-D projecting therefrom. Casing 70C is comprised of a polymeric film and can be formed in the same way and from the same materials as casing 70B previously discussed. Intake port 64B is coupled with manifold section 224 while exhaust ports 65B1-65B4 are attached to the free end of sleeves 226A-D, respectively. Each exhaust port 65B1-65B4 can be the same as exhaust port 65B previously discussed. Attached to each exhaust port 65B1-65B4 so as to be received within a corresponding sleeve 226A-D is a filter 74B 1-B4, respectively. Each filter 74B 1-B4 can be the same as filter 74B previously discussed.

During use, intake port 64B is coupled with gas line 68 (FIG. 1) for receive gas either directly from container 16 or through condenser system 36. In turn, each exhaust port 65B1-65B4 is coupled with a corresponding gas line section which couples with transfer line 180 and which feeds to vacuum pump 185. As such vacuum pump 185 can apply a negative pressure to each of exhaust port 65B 1-65B4 and corresponding filters filter 74B 1-B4. Filters 74B1-B4 can be used concurrently to filter the gas. Alternatively, sleeves 226A-D can be selectively clamped closed to prevent gas from passing therethrough and then subsequently opened. As such, filters 74B1-B4 can be used consecutively to filter gas therethrough. It is appreciated that filter assembly 66F can be formed with 2, 3, or 5 or more sleeves with each sleeve housing a separate filter 74.

Returning to FIG. 1, coupled with transfer line 180 at spaced apart locations between filter assembly 66 and vacuum pump 185 is a valve 184, a trap 186 and a pressure sensor 188. Valve 184 is used to selectively release gas from gas line 180 when the pressure therein becomes positive or exceeds a predetermined positive value. For example, if vacuum pump 185 stops operating or transfer line 180 becomes closed or otherwise blocked, gas pressure can build within casing 70 of filter assembly 66, condenser bag 40 and/or container 16, as applicable. As previously discussed, elevated pressures within these structures can cause the polymeric film and/or the seams formed therewith to rupture, thereby allowing contamination to enter the sterile environment and eventually contaminate fluid 24.

Valve 184 operates as a pressure release valve to automatically release the gas pressure so that there is no failure in the system. To that end, valve 184 can comprise a passive valve such as a check valve including a ball check valve, diaphragm check valve, or swing check valve that automatically opens when a positive pressure or a predetermined positive pressure is reached. The gas passes through valve 184 and is then exhausted to the environment. In other embodiments, valve 184 can comprise an active valve that is operated by computer processor 190. For example, valve 184 can comprise an electric valve, pneumatic valve, or hydraulic valve which is electrically coupled with computer processor 190. Processor 190 is programmed so that when the pressure within gas line 180 becomes positive or exceeds a predetermined positive value as measured by pressure sensor 188, computer processor 190 opens valve 184 until the pressure within gas line 180 drops to an acceptable value. Valve 184 can then be automatically closed. The process can then be repeated as the pressure within gas line 180 again begins to elevate. In other embodiments or in conjunction with the above, valve 184 can be configured to automatically open when a positive pressure or a predetermined pressure is detected within gas line 180 such as through pressure sensor 188 (discussed below) or some other pressure sensor coupled with gas line 180. In still another embodiment, valve 184 can comprise a manual valve such as a standard ball or gate valve which is manually opened when the pressure within gas line 180 exceeds a predetermined valve.

Trap 186 is optional and is used to collect fluid that may condense within gas line 180. The condensed fluid retrieved from trap 186 can be held in a storage vessel 192 for subsequent disposal or processing or can be directly fed back to container 16 through a fluid line connected to trap 186. Trap 186 helps to ensure that fluid condensed in transfer line 180 is not unintentionally exhausted from the system and that the condensed fluid does not destruct the downstream values or pumps.

As previously mentioned, pressure sensor 188 senses the pressure within transfer line 180. Pressure sensor 188 can be wired to computer processor 190. Alternatively, readings from pressure sensor 188 can be conveyed to computer processor 190 via a transmitter 187. Pressure sensor 188 can be used to control the operation of valve 184 as discussed above.

Figure 7:
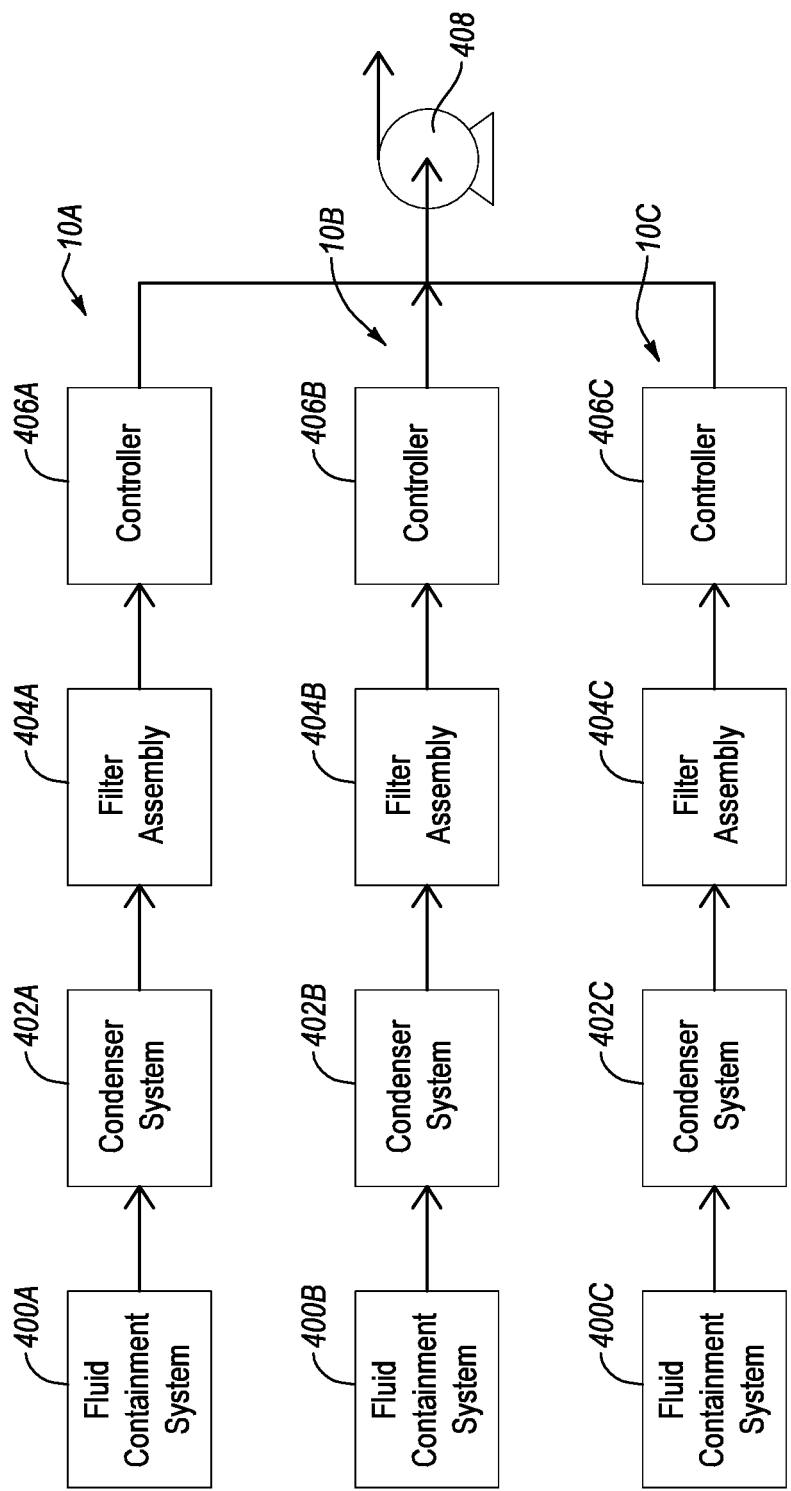
FIG. 7 is a schematic view showing a plurality of different fluid processing systems 10 operating with a central vacuum source.

In one examplary embodiment, a central vacuum source can be concurrently coupled in parallel to a plurality of different fluid processing systems. For example, depicted in FIG. 7 is a system that comprises central vacuum source 408 coupled in parallel to fluid processing systems 10A-10C. Central vacuum source 408 can comprise one or more individual vacuum pumps 185, as discussed above, that operate together to form a single vacuum source. In one application the vacuum source 408 can be run continuously. Each fluid processing system 10A-10C comprises a fluid containment system 400, an optional condenser system 402, a filter assembly 404 and a controller 406.

Fluid containment system 400 can comprise container 16, a means for mixing the fluid within container 16 and the other elements and/or alternatives discussed above with regard to container 16. Condenser system 402 can comprise condenser system 36 and the alternatives thereof discussed above and which operates with fluid containment system 400 in the same way that condenser system 36 operates with container 16. Filter assembly 404 comprises filter assemblies 66 and the alternatives thereof discussed above which operates with condenser system 402 or directly with fluid containment system 400 in the same way that filter assemblies 66 operate with condenser system 36 or container 16. Controller 406 comprises the alternative control systems discussed above, such as processor 190, valve 182 and pressure sensor 33, which are used to automatically regulate the application of the partial vacuum from central vacuum source 408 to filter assembly 404 based on the gas pressure within fluid containment system 400 or some other predetermined value.

In contrast to having a separate controller 406 for each fluid processing system 10A-10C, a single controller 406 could regulate all of fluid processing system 10A-10C. Furthermore, although FIG. 7 shows three fluid processing systems 10A-10C operating with central vacuum source 408, in other embodiments 2, 4, 5, 6 or more fluid processing systems could operate with a single central vacuum source 408. The above configuration provides for a single, continuous vacuum source that can be shared across a plurality of work stations in a facility and thus eliminates the need for separate vacuum pumps.

Tests were conducted to determine the expected improvements to gas flow capacity through filters that could be achieved if a vacuum device were applied to the exhaust gas filter of a bioreactor.

Materials & Methods:

Samples of two different cartridge filter types were selected for the purpose of comparison of normal flow verses vacuum assisted gas filtration: 1) Meissner filter using polyvinyl difluoride (PVDF) having 0.2 micron pore rating and 2.5 inch in designated length and 2) Zenpure filter using polyethylene (PE) having 0.2 micron pore rating and 2 inch in designated length. The filters were housed within a stainless steel filter housing. To mimic the off-gas flow of a bioreactor bag, a 500 slpm Alicat mass flow controller (MFC) was used to meter a known flow rate of air into the stainless steel filter housings. Pressure gauges were placed both before the filter (between MFC and filter) and after the filter (between the filter and the vacuum pump). Prior to filter testing, the filtration assembly was evaluated without a filter cartridge loaded to verify that backpressure inherent in the assembly would not distort the results and also with the exhaust line closed to confirm the assembly was leak proof. One of each filter was tested under normal gas flow where the gas passing through the filter was simply exhausted to the atmosphere. One of each filter was also tested with a Becker VT4.40 rotary vane vacuum pump applying a negative pressure to the outlet port of a the filter housing. The vacuum pump generated 23 inHg of vacuum (−11.3 psi) of vacuum at dead head (full vacuum, no flow). During testing of actual gas flow the differential between inlet and outlet of the filter was typically less than 3 psi (delta).

Figure 8:
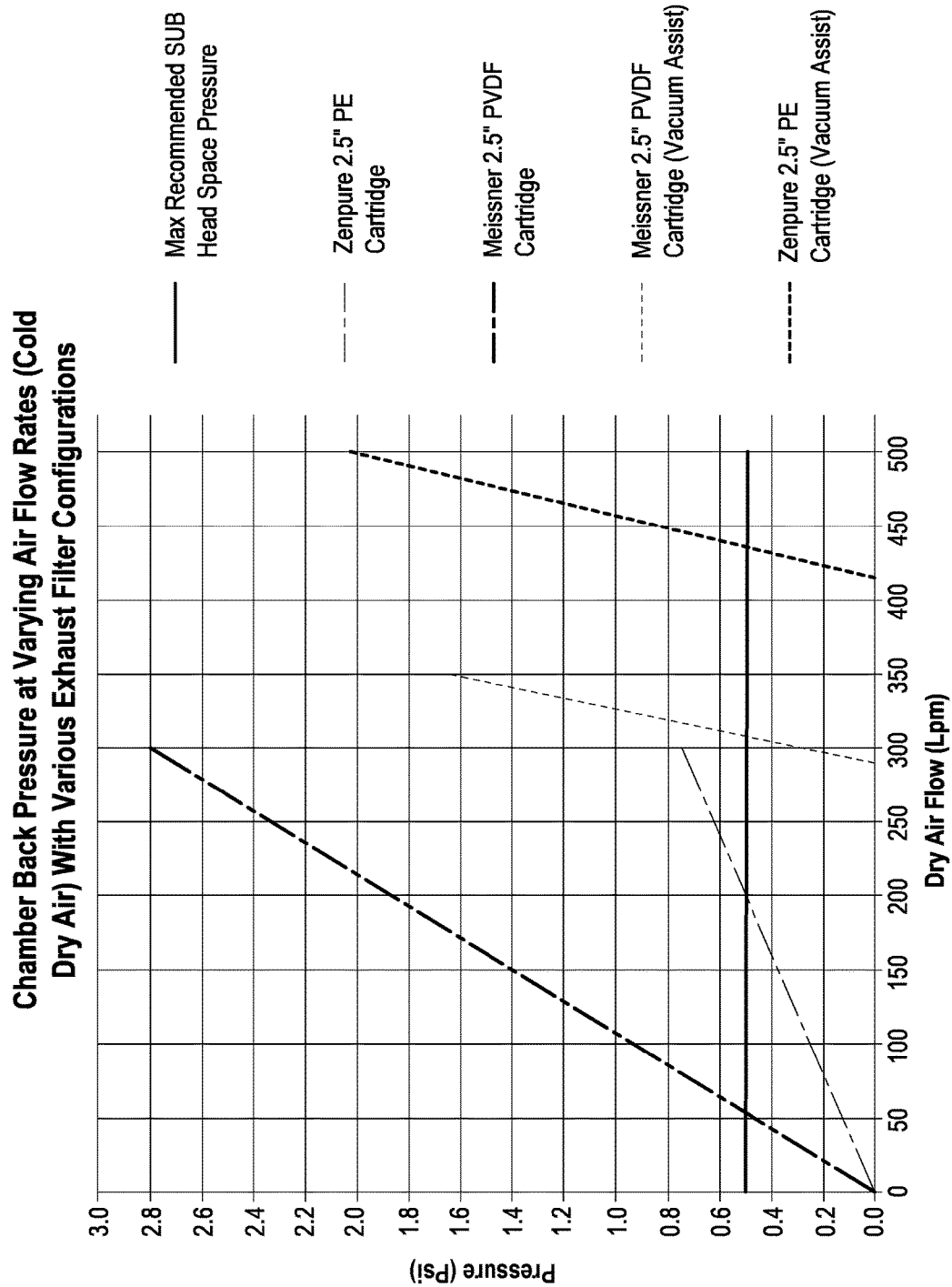
FIG. 8 is a chart showing comparative data of gas flow through filters with and without applied negative pressure.

Results:

The results are set forth in the chart presented as FIG. 8 and are based upon ambient conditions of 12.35 psi absolute pressure and a room temperature of 75° C. The PVDF Meissner filter yielded a significant improvement with the added vacuum. Specifically, at a 0.5 psi backpressure, the gas flow through the filter increased from 208 slpm up to 430 slpm which is an increase of 207%. The PE Zenpure filter yielded an even more significant improvement. Specifically, at a 0.5 psi backpressure, the gas flow through the filter increased from 58 slpm to 290 slpm which is an increase of 500%.

The results demonstrate significant improvements over normal flow filtration and do confirm the potential for both cost savings and improved performance. Operating this system at sea level would likely improve performance up to 16% compared to the 4200 foot elevation of the test laboratory. It should also be recognized that a larger vacuum pump capable of a larger mass flow rate will prove beneficial during scale-up and likely be able to support >1000 slpm of airflow with a 10 inch filter length while operating a back pressure less than the desired process limit of 0.5 psi backpressure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for filtering a gas, the method comprising:
    delivering a gas into a compartment of a gas filter assembly, the compartment being at least partially bounded by a casing comprised of a flexible sheet of polymeric film; and
    applying a partial vacuum to the gas filter assembly so that the partial vacuum assists in drawing the gas through a porous filter body of the gas filter assembly that is at least partially disposed within the compartment of the gas filter assembly.

2. The method for filtering as recited in claim 1, further comprising sparging the gas through a liquid within a compartment of a container prior to delivering the gas into the compartment of the gas filter assembly.

3. The method for filtering as recited in claim 2, wherein the container comprises a flexible, collapsible bag.

4. The method for filtering as recited in claim 1, further comprising automatically regulating the application of the partial vacuum based on a pressure reading of the gas upstream of the gas filter assembly.

5. The method for filtering as recited in claim 2, further comprising regulating the application of the partial vacuum based on a sensed value for gas pressure within the container.

6. The method for filtering as recited in claim 2, wherein the liquid comprises a culture that includes media and cells or microorganisms suspended therein and the container comprises a bioreactor.

7. The method for filtering as recited in claim 1, further comprising passing gas through a condenser assembly to remove moisture from the gas prior to delivering the gas into the compartment of the gas filter assembly.

8. The method for filtering as recited in claim 7, wherein the condenser assembly comprises a flexible bag through which the gas is passed.

9. The method for filtering as recited in claim 2, wherein the filter body of the gas filter assembly has a pore size of 0.22 micometers (μm) or smaller.

10. The method for filtering as recited in claim 1, further comprising maintaining a pressure differential between a gas intake port of the gas filter assembly and a gas exhaust port of the gas filter assembly in a range between 0.5 kPa and 50 kPa, the gas exhaust port having the partial vacuum applied thereto.

11. The method for filtering as recited in claim 1, further comprising activating a heating element secured to the gas filter assembly to heat the gas passing through the gas filter assembly.

12. The method for filtering as recited in claim 1, wherein the casing of the gas filter assembly comprises a flexible, collapsible bag.

13. A system for filtering a gas comprising:
    a container having a compartment configured to hold a liquid;

a first gas filter assembly coupled with the container so that a gas can pass from the compartment of the container to the first gas filter assembly, the first gas filter assembly comprising:
  a casing comprised of a flexible polymeric film bounding a compartment; and
  a first filter body being at least partially disposed within the compartment of the casing; and
a first vacuum pump coupled with the first gas filter assembly so that when the first vacuum pump is activated a partial vacuum is produced that assists in drawing gas from the container through the first gas filter assembly.

14. The system as recited in claim 13, wherein the container comprises a flexible, collapsible bag.

15. The system as recited in claim 13, wherein the casing of the first gas filter assembly comprises a flexible, collapsible bag.

16. The system as recited in claim 13, further comprising:
  a pressure sensor positioned to sense a gas pressure within the compartment of the container; and
  a computer processor in electrical communication with the pressure sensor and the first vacuum pump.

17. The system as recited in claim 13, further comprising:
  a pressure sensor positioned to sense a gas pressure within the compartment of the container;
  a control valve disposed in fluid communication between the first gas filter assembly and the first vacuum pump; and
  a computer processor in electrical communication with the pressure sensor and the control valve.

18. The system as recited in claim 13, further comprising a second vacuum pump coupled with the first gas filter assembly.

19. The system as recited in claim 13, further comprising a condenser assembly coupled with the container so that gas passing from the container to the first gas filter assembly passes through the condenser assembly, the condenser assembly comprising:
  a condenser bag coupled with the container and the first gas filter assembly; and
  a condenser panel disposed adjacent to the condenser bag and coupled with a chiller.

20. The system as recited in claim 13, wherein the first filter body has a pore size of 0.22 micometers (μm) or smaller.

* * * * *